United States Patent [19]

Armstrong et al.

[11] 4,342,667

[45] Aug. 3, 1982

[54] PROCESS FOR PREPARING A SILVER CATALYST

[75] Inventors: William D. Armstrong, South Norwalk, Conn.; Charles N. Winnick, Ridgewood, N.J.

[73] Assignee: The Halcon SD Group, Inc., New York, N.Y.

[21] Appl. No.: 23,575

[22] Filed: Mar. 26, 1979

[51] Int. Cl.$^3$ .......................... B01J 23/04; B01J 23/50
[52] U.S. Cl. .................................... 252/476; 252/475; 549/534
[58] Field of Search ........................ 252/463, 475, 476

[56] References Cited

U.S. PATENT DOCUMENTS

| 2,424,083 | 7/1947 | Finch et al. | 252/476 X |
| 2,920,052 | 1/1960 | Martin | 252/463 |
| 3,563,913 | 2/1971 | Krijger et al. | 252/463 |
| 3,962,136 | 6/1976 | Nielsen et al. | 252/476 X |
| 4,007,135 | 2/1977 | Hayden et al. | 252/476 X |
| 4,033,903 | 7/1977 | Maxwell | 252/476 |
| 4,066,575 | 1/1978 | Winnick | 252/476 X |
| 4,248,740 | 2/1981 | Mitsuhata et al. | 252/463 |

FOREIGN PATENT DOCUMENTS 2128378 10/1972 France .
2002252 2/1979 United Kingdom .

*Primary Examiner*—W. J. Shine
*Attorney, Agent, or Firm*—William C. Long; Riggs T. Stewart; Harold N. Wells

[57] ABSTRACT

A supported silver catalyst for oxidation of ethylene to ethylene oxide is prepared by impregnation of the support, activation, and solvent washing, with each step being carried out at a relatively low temperature. Silver so deposited has an average particle diameter of about 0.5–0.7 microns and is capable of being promoted by post-deposition of alkali metals such as cesium, rubidium, and potassium.

1 Claim, No Drawings

PROCESS FOR PREPARING A SILVER CATALYST

PRIOR ART

The invention relates to the oxidation of ethylene with molecular oxygen over a catalyst to produce ethylene oxide. The catalyst used must promote the oxidation of ethylene to ethylene oxide, while minimizing the burning of the ethylene to carbon dioxide and water. Such a catalyst is said to have a high selectivity to the production of ethylene oxide. Typically, the catalyst used for oxidation of ethylene to ethylene oxide is a supported silver catalyst.

Generally, a supported silver catalyst in commercial operation will convert approximately 15 to 30% of the ethylene passing through the reactor, with a selectivity to ethylene oxide in the range of about 60% to about 80%. Since the conversion of ethylene is a minor fraction of that fed, a commercial plant will ordinarily recover the ethylene oxide from the reactor effluent and then recycle the unreacted gases back to the reactor until essentially all of the fresh ethylene has been converted to ethylene oxide or by-products.

It has been found that adding certain materials to the supported silver catalyst has the effect of improving selectivity of the catalyst to ethylene oxide. Recently, catalysts containing alkali metals, in particular, potassium, cesium, and rubidium have been disclosed, for example in U.S. Pat. No. 3,962,136 in which the alkali metals are co-deposited with the silver and in quantities between $4 \times 10^{-5}$ and $8 \times 10^{-3}$ gram equivalent weight per kilogram of the total catalyst, and in U.S. Pat. No. 4,066,575, where the alkali metals are post-deposited in amounts from $4 \times 10^{-5}$ to $4 \times 10^{-3}$ gram atoms per kilogram of catalyst. The alkali metals are included in the silver catalyst in quite small amounts and, data presented in some of the patents suggest that larger amounts of the alkali metals have an undesirable effect on the selectivity to production of ethylene oxide.

Many techniques for the preparation of supported silver catalysts for use in oxidation of ethylene to ethylene oxide have been disclosed in the prior art. With respect to the present invention, the following patents are considered to be material. Silver is normally deposited on the surface of a support from a silver compound, such as a silver salt of a carboxylic acid. Reduction of such silver salts is generally carried out either chemically or by thermal decomposition. U.S. Pat. No. 2,424,083 granted to Finch, et al. shows the use of ammonia and a reducing agent such as glucose or aldehyde to carry out the reduction of silver nitrate, thereby depositing a thin film of silver on a support while it is immersed in the silver solution. The patentees state that silver is deposited by this technique in much lower quantities than are typical of other methods. It appears from the disclosures in the patent that the temperature at which the deposition of silver was carried out was not considered to be critical. Promoters including alkali metals and alkaline earth metals were considered optional. Addition of sodium after the silver had been laid down on the support surface was suggested as one method of application, but derivation of sodium from the silvering solution was said to be particularly effective.

In U.S. Pat. No. 3,563,913, Krijger, et al., show the use of reducing agents such as amines and preferably polyhydric alcohols for the use in the deposition of silver. A silver solution, including a reducing agent, was used to impregnate a support and then the silver compound was reduced at a high temperature (preferably 400°–800° C.) in a fluidized bed. The patentees' method particularly produced a very rapid drying and decomposition of the silver compounds (2–30 seconds) which was said to be superior.

Nielson, in U.S. Pat. No. 3,702,259, disclosed the preparation of a fine dispersion of silver particles on a support by means of a technique involving the use of organic amine solubilizing/reducing agents such as ethylene diamine and ethanolamine. Silver was generally present as a salt of a carboxylic acid such as silver lactate. The impregnated support was heated at a temperature of 100°–375° C., preferably 125° C.–325° C., to decompose the silver compound and deposit silver particles on the support. The examples generally showed the use of gradually rising temperatures for this purpose. The patentee stated that lower temperatures were not preferred since incomplete decomposition of silver occurred. Other patents commonly assigned with the Nielson '259 patent and disclosing substantially the same solubilizing/reducing agents, include U.S. Pat. Nos. 3,962,136, 4,010,115, and 4,012,425.

In still another recent U.S. Pat. No. 4,130,570, issued to Boreskov, et al., the use of ethylene glycol as a reducing agent was disclosed in a method for preparation of a silver-cadmium catalyst for ethylene oxide production in a fluidized bed. In the patentees' technique, a suspension of particles of silver and cadmium carbonates is impregnated into an alumina carrier while the temperature is gradually increased up to 60°–100° C. Subsequent drying of the impregnated carrier is carried out at a temperature from 120°–150° C., which is stated to reduce silver carbonate to metallic silver, but which reduces calcium carbonate only partially to the oxide, if reduced at all.

Reactivation of used (at least partially deactivated) ethylene oxide catalysts has been interest in recent years. For example, U.S. Pat. No. 4,051,068 to Rebsdat, et al., discloses the impregnation of a used supported silver ethylene oxide catalyst with 1–1000 ppm by weight of cesium or rubidium. The used catalyst is impregnated with a solution of alkali metal salts dissolved in small amounts of water and then mixed with relatively large amounts of aliphatic alcohols. The patentee considered that the temperature of the subsequent drying step was not critical, but the preferred temperature of 90°–110° C., apparently was selected principally to facilitate evaporation of the alcohol and water, rather than with respect of any effect on the silver particles.

In a similar disclosure, Maxwell in U.S. Pat. No. 4,033,903 disclosed the impregnation of a used silver catalyst with potassium, cesium, or rubidium from an alcohol solution.

A patent of interest with respect to one aspect of the present invention is French Pat. No. 2,128,378 (equivalent to U.S. Ser. No. 119,829, filed Mar. 1, 1971) in which supported silver catalysts for ethylene oxide production prepared by impregnating a support with a solution of a silver salt and an organic amine are disclosed to have improved activity when heated to 175°–300° C. and then washed with methanol or ethanol. It is stated by the patentees that they presume the washing has the effect of removing organic amines and potassium nitrate left on the surface during the deposition of silver. The examples indicate that a catalyst prepared by heating at 150° C. to decompose silver oxalate gave relatively poor conversion of ethylene to ethylene oxide and which was improved by the heating and washing of the invention.

Despite the advances in the art as discussed above, further improvements in ethylene oxide catalysts have been sought. The present invention, as disclosed below, includes an improved ethylene oxide catalyst and its method of preparation.

SUMMARY OF THE INVENTION

The catalyst of the invention is characterized in particular by its method of preparation, which is carried out at relatively low temperatures compared to methods of the prior art. A suitable support is impregnated with a solution of a decomposable silver compound or complex at a temperature at or below 110° C., preferably below 75° C., most preferably below 65° C. The impregnated support is drained free of excess solution and then held at a temperature not below about 85° C. or above about 200° C. and preferably between about 100° C. and 150° C., and most preferably about 125° C. for sufficient time to permit substantially all of the silver compound to be decomposed and the silver deposited on the support. Thereafter, the residual solution preferably is washed from the silver-containing support with a suitable solvent such as ethanol, until at least 85% of the residue is removed, preferably 95%, and most preferably more than 98%. The washed silver-containing support is dried at a temperature not in excess of 100° C., preferably in the range of 40°–80° C., leaving a supported silver catalyst which is capable of being promoted by post-impregnation of the dried catalyst with a solution of an alkali metal.

The catalyst of the invention consists essentially of a support having a surface area in the range of 0.02–2 m$^2$/gm, preferably 0.1–1 m$^2$/gm and most preferably 0.25–0.5 m$^2$/gm and an average pore diameter of 0.5–50 microns preferably 0.5–15 microns, and most preferably 1.5–5 microns. Silver is deposited on the support by the low temperature technique outlined above, which produces silver particles on the surface characterized by having an average diameter in the range of 0.5–0.7 microns and in being capable of being promoted by post-deposition of alkali metals selected from the group consisting of cesium, rubidium, and potassium.

Catalysts produced by the low temperature deposition technique summarized above are capable of promotion by post-deposition of alkali metals in contrast to methods typical of the prior art which generally are carried out at higher temperatures and which produce silver particles not generally promotable by post-deposition of alkali metals.

DESCRIPTION OF THE PREFERRED EMBODIMENTS

Catalyst Composition

Supported silver catalysts for oxidation of ethylene with molecular oxygen to ethylene oxide are widely known in the art. In such catalysts according to the present invention. The silver is normally supported on an inert material having relatively low surface area, i.e., about 0.02–2 square meters per gram, preferably 0.1–1 square meters per gram, and most preferably 0.25–0.5 square meters per gram. The support should have an average pore diameter of 0.5–50 microns, preferably 0.5–15 microns, and most preferably 1.5–5 microns and a pore volume of about 0.2–0.5 cc/gm. Surface area is the value measured by the BET technique (the Brunauer, Emmet, and Teller method, J. Am. Chem. Soc., 60, 309–16 (1938)) and the pore volume is obtained by the mercury absorption method (Drake & Ritter, Inc. Eng. Chem. Anal Ed, 17,787 (1945)). While a number of supports may be used, including alumina, silica, mixtures of silica and alumina, silica-alumina, and silicon carbide, preferably mixtures of silica and alumina or pure alumina is used.

Typical supports which may be used are the low surface area, alpha-alumina-containing materials manufactured by the Norton Company, such as those shown in the following table.

Since the oxidation reaction is highly exothermic, the catalyst particles are commonly disposed within relatively small diameter tubes from which the heat of reaction can be readily dissipated. Consequently, the particles must be within a fairly narrow size range in order to obtain suitable performance in such reactors. The supports are commonly formed into regular shapes, i.e. spheres, rings, and the like, and generally are in the range of 4.76 mm to 7.94 mm (3/16" to 5/16") equivalent diameter.

The finished catalyst ordinarily will contain an amount of silver in the range of about 5–25% by weight of the total catalyst.

| Designation | SA-5203 | SA-5218 | SA-5121 | SA-5223 | SA-5252 |
| --- | --- | --- | --- | --- | --- |
| Alumina, wt % | 86.9 | 86.1 | 89.4 | 87.2 | 93.1 |
| Silica, wt % | 11.6 | 12.0 | 9.3 | 11.1 | 5.6 |
| Apparent porosity, % | 40–45 | 38–42 | 41–46 | 34–38 | 51–57 |
| % of pores with diam. in range of (in microns): | | | | | |
| 1–10 | 20 | — | 15 | 20 | 50* |
| 10–100 | 70 | 80 | 75 | 60 | 34 |
| >100 | 10 | 20 | 10 | 20 | 6 |
| Surface area, sq. meters/gm | 0.02–0.08 | 0.005–0.04 | 0.02–0.07 | 0.02–0.06 | 0.2–0.5 |
| Pore volume, cc/gm. | 0.21 | 0.19 | 0.22 | 0.17 | 0.31 |

*10% of pores have diameters of >1.0 micron.

Greater amounts of silver are unduly expensive, while lesser amounts are not desirable, since the useful life and activity of the catalyst are reduced. Preferably the amount of silver is about 10–20% by weight, and typically 14–17% by weight is selected.

The catalyst of the invention will contain at least one alkali metal selected from the group of cesium, rubidium, and potassium post-deposited on a previously prepared supported silver catalyst. The amount of alkali metal based on the finished catalyst will be within the range of about 20 to about 200 ppm (wt) and preferably within the range of about 35 to about 75 ppm (wt).

Other materials known to have a promotional effect may be included in the catalyst, such as members of Group IIa of the Periodical Table, such as barium, calcium, strontium, and magnesium, which if used are present in amounts which are typically in the range of 10–3000 ppm by weight as metal, and preferably in the range of 100–1000 ppm by weight, based on the total catalyst.

CATALYST PREPARATION

A number of methods of preparing ethylene oxide catalysts have been disclosed in the art, for example U.S. Pat. No. 4,066,575 in which post-deposition of alkali metals is associated with a silver catalyst prepared by impregnation and activated by heating in an oxygen-free atmosphere. The catalysts prepared by such a method are less stable than is desired for long-term service. The improved method of catalyst preparation to be discussed below is capable of obtaining the benefits of minor promotional amounts of alkali metals and retaining such benefits in commercial operation.

Preferably, the support particles are impregnated by soaking them in a silver-containing solution containing the desired quantities of silver and selected Group IIa promoters, if any, until the desired quantity of catalytic materials has been absorbed. The amount of silver used in impregnating solutions will vary, but typical solutions contain from 5–50 wt % silver in the form of a silver compound or complex, such as silver acetate, benzoate, oxalate, malonate, succinate, glutarate, and maleate. Silver lactate is particularly preferred. In U.S. Pat. No. 4,066,575 is a typical example of an impregnating solution, and which contains 55 to 73 wt % silver lactate, 15 to 45 wt % lactic acid, 0.05 to 0.3 wt % barium acetate, 0 to 0.5 wt % hydrogen peroxide (an oxidizer used to prevent premature reduction of silver), and from 0–20% water. Optionally, the solution may contain a non-nitrogenous reducing agent such as aldehydes, alcohols, polyols, keto alcohols and the like. Polyols such as ethylene glycol and glycerol are preferred. Such reducing agents facilitate the relatively low temperature impregnation and activation procedures characteristic of the present invention.

As will be understood by those skilled in the art, the concentration of the metals in the impregnating solution will affect the amount of metals deposited, as also will the nature of the support and the time and temperature at which the impregnation is carried out. These variables will be adjusted to provide the desired amount of metals on the support.

The catalyst support particles are immersed in a solution for about 1–60 minutes at temperatures below about 110° C. It is characteristic of the process that lower temperatures than those usually preferred in the prior art are used. Preferably the impregnation is carried out at temperatures below 75° C., most preferably below 65° C. The period of immersion may be adjusted in order to obtain the desired amount of absorption of catalytic materials into the support particles. Typically, immersion of 20 minutes at a temperature of about 60° C. is used. A single immersion ordinarily will be sufficient to deposit the desired amount of silver under the conditions described above. However, multiple immersions, with or without intermediate drying, may be employed. Alternatively, the amount of solution could be adjusted to be entirely absorbed onto the support with no free liquid remaining.

After completion of the impregnation of the particles, they are removed from any residual solution and then dried and activated at a temperature not below about 85° C. or above about 200° C., and preferably between about 100° C. and 150° C. Typically a temperature of about 125° C. is used. The activation process is continued for a period of time sufficient to decompose the silver compound or complex and to deposit finely divided silver particles on the surface. It is common practice of the prior art to heat the particles gradually in the presence of air to temperatures in the range of 200°–300° C. or more and to retain that temperature until the activation is complete. It is a particular characteristic of the present invention that the activation step is carried out at relatively low temperatures, as is also true of the remaining steps of the preparation to be described.

It is typical of the prior art that high temperatures are employed during the activation procedure which have the effect of driving off organic residues from the catalyst. Since it is characteristic of the present procedure that low temperature activation of the catalyst is used, in order to remove organic residues a solvent washing step preferably is employed following the activation procedure.

Various solvents may be used including, but not limited to, water, alcohols, ketones, organic acids, and aromatic hydrocarbons. Particularly preferred solvents are water and the lower aliphatic alcohols, such as methanol, ethanol, and isopropanol. The wash procedure is carried out at a relatively low temperature, such as 20°–100° C., although a temperature in the range of 40°–80° C. is preferred. Representative washing procedures are given in the subsequent examples. It will be understood that the factors which govern the effectiveness of such washing include the temperature, solubility of the organic residues in the solvent selected, the amount of residue to be removed, and the completeness of its removal. In general, it is desired that at least 85%, preferably 95%, and most preferably more than 98% of the organic residues left after the low temperature activation step should be removed by solvent washing.

Solvent washing is preferred in the present inventions for removal of organic residues, carried out at relatively low temperatures. High temperature procedures of the prior art served to deposit silver particles on the support while oxidizing or vaporizing the organic residues in a single operation. The present invention carried out the deposition and activation of silver particles and the removal of organic residues in two separate procedures.

It has been discovered that a supported silver catalyst prepared according to the procedure discussed has the ability to be promoted by the subsequent deposition of an alkali metal selected from the group consisting of potassium, rubidium, and cesium. Catalysts prepared by heating to a high temperature above 300° C. in air in order to activate them and to remove organic residues, have been found to be unreceptive to post-deposition by alkali metals. The procedure of U.S. Pat. No. 4,066,575 wherein the catalyst is heated to 300°–400° C. for activation in an essentially oxygen-free atmosphere also has been found to provide a supported silver catalyst which is receptive to post-deposition by alkali metals. That procedure is distinctly different from the present procedure which employs a sequential process using a low temperature activation not below about 85° C., and preferably between about 100° C. and 150° C., and solvent washing of residues in order to provide a supported silver catalyst receptive to post-deposition of alkali metals.

The post-impregnation step is carried out with a solution of an alkali metal compound. Hydroxides, carbonates, acetates, and nitrates of the metals are preferred. Halides, sulfates, and sulfides of the metals are less desirable forms. The alkali metal compounds are dissolved in a suitable solvent, preferably water or a lower aliphatic alcohol such as ethanol. The temperature of impregnation is not critical and typically it will be carried out at near ambient temperatures and for a period of time sufficient to impregnate the silver catalyst with the desired amount of alkali metal. Following the impregnation, the catalyst will be removed from the impregnating solution and dried in air at a temperature below 150° C., preferably below 125° C., and most preferably about 100° C.

PROCESS OF USE

The oxidation of ethylene to ethylene oxide by molecular oxygen over a supported silver catalyst usually takes place in the range of about 150°–400° C. Typical commercial operations are carried out in the range of 200°–300° C. Lower temperatures are generally preferred in order to avoid excessive combustion of ethylene to carbon dioxide and water, which in effect lowers the selectivity of the process to production of the desired ethylene oxide. The reaction is carried out at a pressure in the range of about 0.5–35 kg/cm² gauge. The feed mixture typically will contain in the range of about 0.5–20 mol % ethylene, 3–15 mol % oxygen, and the remainder inerts such as carbon dioxide, nitrogen, methane, ethane, argon, and the like. The inert gases have an important effect on the performance of the catalyst system in particular, by assisting in the removal of the substantial heat of reaction.

Although the selectivity of the reaction under the conditions described and with the catalyst of the invention typically will be in the range of about 74 to 78%, the amount of ethylene contained in the feed which is actually converted, will be relatively small, say about 5 to 30% of the feed ethylene. Consequently, the reactor effluent is treated to remove ethylene oxide and the remaining unreacted gases are returned to the reactor.

It has been found that the catalyst of the invention, containing small amounts of post-deposited alkali metals, produces a significantly improved selectivity to ethylene oxide compared to the same catalyst without post-deposited alkali metals, as will be seen later, and also compared to a similar catalyst activated at high temperatures in air in the manner of the prior art and which will be seen to be unresponsive to post-deposition of alkali metals.

The following example illustrates a preferred method of preparing the catalyst of the invention.

EXAMPLE 1

An impregnation solution is prepared by dissolving 1525 gm of silver oxide in a solution of 100 gm of distilled water and 1800 gm of 88% lactic acid. The lactic acid water solution is heated to 85° C. and the silver oxide is added in increments with vigorous stirring. Hydrogen peroxide is added to clear the solution of prematurely reduced silver, followed by the addition of 12.0 gm of barium acetate dissolved in water. To the resultant solution is added 700 gm of glycerol and the mixture is cooled to 60° C. The support material (Norton 5552 rings) is preheated to 60° C. and immersed in the solution at 60° C. and held for 20 minutes. The impregnated support is drained and activated by holding at 100° C. in air for 20 hours. The catalyst is washed in enough boiling ethanol (78.5° C.) to cover the support material and after six separate washings with fresh ethanol the organic residues are less than 1% of the total weight of the catalyst. The washed catalyst is then dried for 16 hours at 100° C. The dry catalyst is impregnated with cesium by immersion in a solution containing 0.03% cesium as cesium acetate in an ethanol-water mixture. Finally, the catalyst is dried at 100° C. for 16 hours.

EXAMPLE 2

In order to evaluate the catalyst of Example 1, 2400 grams of catalyst was charged to a reactor consisting of an oil-jacketed vertical tube of 21.8 mm internal diameter and a bed height of 7.5 meters. A feed mixture of 0.2% ethane, 15% ethylene, 7% oxygen, 6% carbon dioxide 0.25 ppm ethylene dichloride and balance nitrogen was fed upward through the reactor at a space velocity of 6000 hr$^{-1}$. The pressure was maintained at 17.6 kg/cm² gauge and the temperature was maintained in the range 240°–250° C.

The results obtained are shown in the following table wherein Catalyst 2 is the catalyst prepared in the manner described in Example 1 on a ring-shaped support (Norton 5552).

TABLE I

| Catalyst | Ag Wt. % | Cs ppm | Reactor Temp. °C. | % EO @ Outlet | % Sel. |
|---|---|---|---|---|---|
| 2 | 17 | 50 | 240 | 1.5 | 75 |

The results of these tests indicate that catalysts prepared according to the invention have good selectivity. For comparison, a commerical catalyst without cesium run in the same manner is found to have a selectivity of 71%. It will be shown in Example 3 that the supported silver catalyst is receptive to alkali metal promotion.

EXAMPLE 3

Two catalysts are prepared as in Example 1 except that they are activated at a temperature of 115° C. Evaluation of the catalysts is carried out as in Example 2 in a reactor consisting of a coiled stainless steel tube of 5.33 mm internal diameter heated by a sand bath. The catalysts are ground to 12–16 mesh and 36 grams having a bulk density of about 0.88 gm/cc is charged to the reactors. A feed mixture of 14% ethylene, 6.7% oxygen, 5.5% carbon dioxide, 0.25 ppm ethylene dichloride and balance nitrogen is passed over the catalyst at a space velocity of 6000 hr−1. The temperature is maintained at 240°–250° C. The results are shown in Table II.

TABLE II

| Catalyst | Ag Wt. % | Cs ppm | Reactor Temp. °C. | % EO @ Outlet | % Sel. |
|---|---|---|---|---|---|
| 3A | 16 | 0 | 241 | 1.5 | 73 |
| 3B | 16 | 50 | 244 | 1.5 | 75 |

For comparison, a commercial catalyst without cesium and tested in the same way gave a selectivity of 73%.

The amount of alkali metal (i.e. cesium, rubidium, and potassium) used in the catalyst of the invention is broadly within the range of 20-200 ppm by weight of the finished catalyst and preferably 35-75 ppm by weight. The following example illustrates that selectivity of the oxidation of ethylene to ethylene oxide is sensitive to the alkali metal content.

EXAMPLE 4

Prepared according to the preparation technique of Example 1, a group of silver catalysts was prepared and tested under the conditions of Example 3 and having a range of cesium content between 25-200 ppm by weight.

The results of the experiment are shown in Table IV, in which it can be seen that the selectivity to ethylene oxide is highest within a fairly narrow range of cesium content.

TABLE III

| Catalyst | Silver Wt. % | Cesium ppm (wt.) | Reactor Temp. °C. | % EO @ Outlet | % Sel. |
|---|---|---|---|---|---|
| 6A | 16.9 | 25 | 241 | 1.5 | 74 |
| 6B | 16.9 | 50 | 244 | 1.5 | 76 |
| 6C | 16.9 | 100 | 260 | 1.5 | 76 |
| 6D | 16.9 | 150 | 263 | 1.5 | 72 |

The temperature employed in the impregnation of the silver compound onto the support should be kept relatively low compared to the teachings of the prior art when preparing a catalyst according to the present invention. It has been found that the selectivity of the finished catalyst is thereby improved, as is shown in the following example.

EXAMPLE 5

The preparation technique described in Example 1 was used to prepare catalysts except that the impregnation temperature was varied. Catalysts so prepared were tested according to the procedure of Example 3, with the following results.

TABLE IV

| Catalyst | Impregnation Temp. (°C.) | Silver Content Wt. % | Cesium Content ppm | % EO @ Outlet | Sel. % |
|---|---|---|---|---|---|
| 7A | 60 | 15 | 50 | 1.5 | 76 |
| 7B | 90 | 13 | 50 | 1.5 | 74 |

The above results may be compared with those of Table I, which also suggests that for impregnation of silver low temperatures are preferred.

EXAMPLE 6

Three catalysts are prepared according to Example 1 except that instead of ethanol being used to wash the activated catalyst, water, methanol and isopropanol are substituted. Upon testing the finished catalyst according to the procedures of Example 3, the following results were obtained:

TABLE V

| Catalyst | Washed Wash | Silver Wt. % | Cesium ppm Wt. | % EO @ Outlet | Sel. % |
|---|---|---|---|---|---|
| 9A | water | 14.9 | 50 | 1.5 | 76 |
| 9B | methanol | 15.1 | 50 | 1.5 | 76 |
| 9C | isopropanol | 15.2 | 50 | 1.5 | 76 |

EXAMPLE 7

A catalyst is prepared according to Example 1 except that it was activated at 115° C., and instead of glycerol, ethylene glycol is substituted. The finished catalyst containing 14.4 wt % silver and 50 ppm by weight cesium is tested by the procedure of Example 3 and a selectivity of 75% to ethylene oxide was obtained at a reactor temperature of 243° C., which produced one and one-half percent ethylene at the outlet of the reactor.

While the use of reducing agents is ordinarily preferred since they accelerate the process of catalyst preparation, nevertheless reducing agents are not essential to preparation of a supported silver catalyst capable of promotion by alkali metals through post-impregnation, as will be seen in the following example.

EXAMPLE 8

A catalyst was prepared according to the procedure of Example 1, except that the impregnation was carried out at 85° C. and no glycerol was used as a reducing agent. The following results were obtained using the procedures of Example 3.

TABLE VI

| Catalyst | Ag Wt. % | Cs ppm | Reactor Temp. °C. | % EO @ Outlet | % Sel. |
|---|---|---|---|---|---|
| 5 | 13.1 | 50 | 233 | 1.5 | 75 |

The method of preparing an ethylene oxide catalyst disclosed herein provides a means by which a freshly-prepared catalyst can be promoted by post-deposition of one or more of the alkali metals cesium, rubidium, and potassium. The following example illustrates that the low temperature procedure of the invention is capable of producing a catalyst which can be promoted whereas a catalyst made by the high temperature activation of the prior art is not so promoted.

EXAMPLE 9

A catalyst was prepared by the method of Example 1, except that the low temperature activation and solvent washing steps are replaced by a conventional one-step activation procedure in which the impregnated catalyst is heated at 200° C. for 2 hours, and finally at 350° C. for 2 hours to complete the activation and to remove any organic residues. Post-impregnation as described in Example 1 is then carried out. The catalyst is tested in a reactor to be described and compared with another catalyst which did not receive post-impregnation with the cesium and the commercial catalyst previously discussed, which also contained no cesium.

The reactor used in these experiments is disclosed by J. M. Berty, Chem. Eng. Prog. 70(5); 78 (1974), and available from Autoclave Engineers, Inc., Erie, Pa. Thirty grams of catalyst were exposed to a feed gas composition and flow rate equal to those of Example 3. Whereas the previous examples reported tests using tubular reactors in which the reactants make only one passage through the catalyst, the reactor used in this Example 9 is constructed so that the reaction products are recirculated in large quantities over the catalysts by an internal mixer. The fresh feed joins the recirculating reaction products and the mixture passes through the catalyst. The products of the reaction are withdrawn in an amount equivalent to the incoming feed. Since the catalyst sees a composition containing more reaction products than the tubular reactors, the selectivity to production of ethylene oxide is somewhat lower than reported in the previous examples. The data in the table below provides the needed comparisons to illustrate that high temperature activation produces a catalyst which is not promotable by post-deposition of the alkali metals.

TABLE VII

| Catalyst | Ag Wt. % | Cs ppm | Reactor Temp. °C. | % EO @ Outlet | % Sel. |
|---|---|---|---|---|---|
| 9A | 15 | 50 | 238 | 1.0 | 70 |
| 9B | 15 | 0 | 231 | 1.0 | 70 |

For further comparison, a commercial catalyst without cesium tested in the same manner is found to have a selectivity of 70%.

The results indicate that a catalyst prepared impregnated according to the process of the invention, but activated at a high temperature is not promoted by post-deposition of cesium. Catalysts 9A and 9B differ only in that one was post-deposited with cesium (9A) while the other (9B) was not. The commercial catalyst gave equivalent results. Therefore, it is concluded that the low temperature activation and solvent washing characteristic of the present invention provides a silver catalyst capable of being promoted by post-deposition of alkali metals.

EXAMPLE 10

Two catalysts are prepared by the method of Example 1 except that one is post-impregnated with rubidium and the other with potassium instead of the cesium of Example 1. Tests are carried out according to the procedures of Example 3 to show that post-deposition with the alkali metal is effective in promoting the selectivity of the supported silver catalysts to the production of ethylene oxide.

The foregoing discussion and examples are intended to provide a detailed description of the invention and its advantages, but not to limit the scope of the invention, which is defined by the claims which follow.

What is claimed is:

1. A process for preparing a catalyst useful in the oxidation by molecular oxygen of ethylene to ethylene oxide comprising:
   (a) impregnating a support with a solution of a silver salt selected from the group consisting of silver acetate, silver benzoate, silver oxalate, silver lactate, silver malonate, silver succinate, silver glutarate, and silver maleate and comprising at least one non-nitrogenous reducing agent selected from the group consisting of alcohols, polyols, and keto alcohols at a temperature at or below 110° C.;
   (b) activating and drying said impregnated support of (a) at a temperature not below 85° C. or in excess of 200° C. for a sufficient time to permit substantially all of the silver in the impregnated solution to be deposited on said support and leaving decomposable residues on said support;
   (c) removing at least 85% of said residues of (b) from said activated support (b) by washing said support with a solvent;
   (d) thereafter post-impregnating the catalyst of (c) with a solution of a compound of one or more alkali metals selected from the group consisting of cesium, rubidium, and potassium and thereafter drying said post-impregnated catalyst.

* * * * *

UNITED STATES PATENT AND TRADEMARK OFFICE
CERTIFICATE OF CORRECTION

PATENT NO.    : 4,342,667
DATED         : August 3, 1982
INVENTOR(S)   : William D. Armstrong and Charles N. Winnick It is certified that error appears in the above-identified patent and that said Letters Patent are hereby corrected as shown below:

Column 4, line 7   -- change "art. In" to -- art, in --;
         line 20  -- change "Inc." to -- Ind. --;

Column 8, line 56  -- change "hr-1." to -- $hr^{-1}$. --;

Column 9, Table V  -- change Catalyst column items "9A, 9B, 9C" to -- 8A, 8B, 8C --.

Signed and Sealed this

Third Day of May 1983

[SEAL]

Attest:

GERALD J. MOSSINGHOFF

Attesting Officer    Commissioner of Patents and Trademarks